United States Patent [19]

Brittain et al.

[11] Patent Number: 4,539,329

[45] Date of Patent: Sep. 3, 1985

[54] 7'-TRIFLUOROMETHYL-SPIRO[IMIDAZOLIDINE-4,3'-INDOLINE]-2,2',5-TRIONES AS ALDOSE REDUCTASE INHIBITORS

[75] Inventors: David R. Brittain; David Brown, both of Macclesfield; Robin Wood, Stockport, all of England

[73] Assignee: Imperial Chemical Industries, plc, Great Britain

[21] Appl. No.: 492,221

[22] Filed: May 6, 1983

[30] Foreign Application Priority Data

May 11, 1982 [GB] United Kingdom ............... 8213651
Nov. 1, 1982 [GB] United Kingdom ............... 8231129

[51] Int. Cl.³ ................. A61K 31/415; C07D 487/10
[52] U.S. Cl. .................................... 514/389; 548/101; 548/309; 548/485; 548/486
[58] Field of Search .............................. 548/309, 101; 424/273 R

[56] References Cited

U.S. PATENT DOCUMENTS 3,767,653 10/1973 Krapcho ..................... 548/486 X
4,053,613 10/1977 Rovnyak et al. ............... 548/486 X
4,386,100 5/1983 Brittain et al. ................. 548/309 X

FOREIGN PATENT DOCUMENTS 28906 5/1981 European Pat. Off. ........... 548/309
65407 11/1982 European Pat. Off. ........... 548/309
66378 12/1982 European Pat. Off. ........... 548/309
2098212A 11/1982 United Kingdom ............... 548/309

OTHER PUBLICATIONS

Yale, H., *J. Med. Chem.*, 1, 121-133 (1959).

*Primary Examiner*—Richard A. Schwartz
*Attorney, Agent, or Firm*—Cushman, Darby & Cushman

[57] ABSTRACT

The invention concerns novel trifluoromethyl derivatives of 1'-halogenobenzyl-spiro[imidazolidine-4,3'-indoline]-2,2',5-trione (I), their pharmaceutically acceptable salts, and non-toxic, biodegradable precursors thereof. The derivatives are potent inhibitors of the enzyme aldose reductase and are useful in treating or preventing certain complications of diabetes. The invention also provides pharmaceutical compositions and processes for the manufacture of the derivatives.

9 Claims, No Drawings

7'-TRIFLUOROMETHYL-SPIRO[IMIDAZOLIDINE-4,3'-INDOLINE]-2,2',5-TRIONES AS ALDOSE REDUCTASE INHIBITORS

This invention concerns novel fluoroalkyl derivatives and more particularly novel trifluoromethyl derivatives of spiro[imidazolidine-4,3'-indoline]-2,2',5-triones which are potent inhibitors of the enzyme aldose reductase. The invention also concerns pharmaceutical compositions and processes for the manufacture of the novel compounds.

The enzyme aldose reductase is responsible in man and other warm-blooded animals for the catalytic conversion of aldoses, for example glucose and galactose, to the corresponding alditols, for example sorbitol and galactitol respectively. Alditols penetrate cell membranes poorly and, once formed, tend to be removed only by further metabolism. As a consequence, alditols tend to accumulate within cells where they are formed, for example in the lens, peripheral nerve tissue and kidney, causing a rise in internal osmotic pressure which may in turn be sufficient to destroy or impair the function of the cells themselves. In addition, raised alditol levels may result in abnormal levels of their metabolites which may themselves impair or damage cellular function. However, the enzyme aldose reductase has a relatively low substrate affinity, that is, it is only effective in the presence of relatively large concentrations of aldose. Such large concentrations of aldose are present in the clinical conditions of diabetes (excessive glucose) and galactosemia (excessive galactose). As a consequence, inhibitors of the enzyme aldose reductase are useful in the reduction or prevention of the development of those complications of protracted diabetes or galactosemia which may be due in part to the accumulation of sorbitol or galactitol respectively. Such complications are, for example, macular oedema, cataract, retinopathy, nephropathy or impaired neural conduction.

It is known from our earlier work that certain 1'-substituted-spiro[imidazolidine-4,3'-indoline]-2,2',5-triones bearing a range of substituents in the benzene ring of the indoline moiety possess useful aldose reductase inhibitory properties (European patent application, publication No. 28906A1). We have now discovered that a narrowly defined, novel group of such compounds containing a 5'-,6'- or 7'-trifluoromethyl substituent possess unexpectedly potent aldose reductase inhibitory properties, and this is the basis for our invention.

According to the invention there is provided a trifluoromethyl spiro[imidazolidine-4,3'-indoline]-2,2',5-trione derivative of the formula I (set out together with other structural formulae given Roman numerals at the end of this specification) wherein the trifluoromethyl substituent in benzene ring A is located at the 5',6' or 7' position; and benzene ring B is dihalogeno-phenyl wherein Ra is fluoro or chloro, Rb is hydrogen and Rc is chloro, bromo or iodo; or Ra is hydrogen and Rb and Rc are independently chloro or bromo; or a salt with a base affording a pharmaceutically acceptable cation; or a non-toxic, biodegradable precursor thereof. The compounds of formula I are derivatives of spiro[imidazolidine-4,3'-indoline]-2,2',5-trione which is numbered as shown in the formula II.

In this specification Ra, Rb et cetera are used to signify generic radicals and have no other meaning.

The compounds of formula I all possess an asymmetric carbon atom, namely the spiro carbon atom at position 4 of the imidazolidine ring. The compounds of formula I therefore exist, and may be isolated, in racemic and optically active forms. This invention encompasses the compounds of formula I in racemic form or in any optically active form which possesses aldose reductase inhibitory properties, it being well known in the art how to prepare optically active forms by resolution of the racemic form, or by synthesis from optically active starting materials, and how to determine the aldose reductase inhibitory properties by the standard tests described hereinbelow.

A preferred value for benzene ring B is 3,4-dichloro-, 3,4-dibromo-, 3-bromo-4-chloro-, 4-bromo- 3-chloro-, 4-chloro-2-fluoro-, 4-bromo-2-fluoro- or 2-fluoro-4-iodo-phenyl.

A preferred group of compounds according to the invention comprises those derivatives of formula III wherein benzene ring B is 4-bromo-2-chloro-, 4-bromo-2-fluoro- or 2-fluoro-4-iodo-phenyl; and one of Rd and Re is trifluoromethyl and the other is hydrogen; together with the pharmaceutically acceptable salts; and the non-toxic, biodegradable precursors thereof.

The term non-toxic, biodegradable precursor includes derivatives of the compounds of formula I defined above in which one or both of the imino hydrogen atoms in the imidazolidine ring is replaced by a biodegradable protecting group known in the art, which group is not inherently toxic and which is capable of removal in vivo (for example by enzymic hydrolysis) to liberate the compound of formula I in sufficient quantity to inhibit the enzyme aldose reductase and without giving rise to pharmacologically unacceptable by-products. Examples of suitable groups for inclusion in biodegradable precursors of compounds of formula I include alkoxycarbonyl, aralkoxycarbonyl, alkoxyoxalyl and 1-(alkanoyloxy)alkyl groups, such as ethoxycarbonyl, t-butyloxycarbonyl, benzyloxycarbonyl, ethoxyoxalyl, methoxyoxalyl and pivaloyloxymethyl groups. In general, the biodegradable precursors are not themselves inhibitors of the enzyme aldose reductase, but are active in vivo by virtue of removal of the bio-degradable protecting radical. It will be apparent, therefore, that by suitable choice of biodegradable protecting groups (for example based on their generally known rates of enzymic degradation) it is possible to produce biodegradable precursors of compounds of formula I whose bioabsorption and distribution properties differ from those of the compounds of formula I.

A preferred non-toxic, biodegradable protecting group is, for example, pivaloyloxymethyl.

Particular salts of compounds of formula I with bases affording a pharmaceutically acceptable cation are, for example, alkali metal or alkaline earth metal salts (such as sodium, potassium, calcium or magnesium salts), aluminium or ammonium salts, or salts with organic bases (such as triethanolamine).

Especially preferred compounds of the invention include (dl)-1'-(4-bromo-2-fluorobenzyl)-5'-trifluoromethyl-spiro[imidazoline-4,3'-indoline]-2,2',5-trione and (dl)- or (d)- 1'-(4-bromo-2-fluorobenzyl)-7'-trifluoromethyl-spiro[imidazolidine-4,3'-indoline]-2,2'-5-trione, or the pharmaceutically acceptable salts or non-toxic, biodegradable precursors thereof.

The novel compounds of formula I may be obtained by any process known in the art for the manufacture of structurally analogous compounds. Such processes are provided as a further feature of the invention and are illustrated by the following presently preferred procedures in which Ra–Re have any of the meanings defined above:

(a) Reacting an indoline-2,3-dione of the formula IV with an alkali metal cyanide, and ammonium carbonate or carbamate.

A suitable alkali metal cyanide is, for example, sodium or potassium cyanide.

This process is an example of the Bucherer-Bergs synthesis of imidazolidine-2,4-diones (hydantoins) which is well known in the art (see E Ware in *Chemical Reviews,* 1950, 46, 422–425). The process may therefore proceed through a hydroxynitrile of the formula V and/or an amino-nitrile of the formula VI.

These intermediates are not in general sufficiently stable to be isolated. However, they may be generated in process (a), for example, by reaction of a compound of formula IV with hydrogen cyanide to give V followed by reaction with ammonium carbonate or carbamate. Similarly, a compound of formula IV may be reacted with ammonia and hydrogen cyanide to give VI, followed by reaction with carbon dioxide, conveniently provided by ammonium carbonate or carbamate.

The process is generally performed in a suitable solvent or diluent, for example in a (1–4C)alkanol such as methanol or ethanol, or in ethylene glycol or diethylene glycol, preferably containing water, and at a temperature in the range, for example 20°–100° C.

The ammonium carbonate or carbamate may if necessary be formed in situ in conventional manner.

The starting materials of formula IV may be obtained by conventional procedures of indole chemistry. For example, they may be obtained by reacting the appropriate indoline-2,3-dione with a benzyl chloride or bromide in the presence of a base, such as sodium or potassium hydroxide or carbonate, in N,N-dimethylformamide or dimethyl sulphoxide at 20°–40° C.

(b) Reacting a compound of the formula VII wherein Rf is acyl or tri-[(1–4C)alkyl]silyl with ammonium carbonate or carbamate.

A particular value for Rf when it is acyl is, for example, (1–6C)alkanoyl such as acetyl or propionyl, phenylsulphonyl, toluene p-sulphonyl, benzoyl or benzyloxycarbonyl.

A particular value for Rf when it is tri-[(1–4C)alkyl]silyl is, for example, trimethylsilyl.

Process (b) is a modification of process (a) hereinbefore and consequently similar reaction conditions may be used. Similarly, the ammonium carbonate or carbamate may be formed in situ if desired.

The starting materials of formula VII may be made by conventional procedures. Thus, those compounds of formula VII wherein Rf is acyl may be conveniently obtained, for example, by reacting an indoline-2,3-dione of formula IV with the appropriate acyl halide (e.g. benzoyl chloride, or benzyl chloroformate) in the presence of sodium or potassium cyanide and sodium or potassium hydroxide, in aqueous methylene chloride at 15°–25° C. Similarly, those compounds of formula VII wherein Rf is tri-[(1–4C)alkyl]silyl may be obtained, for example, by reacting the appropriate indoline-2,3-dione of formula IV with a tri-[(1–4C)alkyl]silyl cyanide (e.g. trimethylsilyl cyanide) at 15°–40° C. in a non-aqueous solvent such as 1,2-dimethoxyethane.

It will be apparent that the above processes produce the compounds of formula I in the form of their base-addition salts, which may readily be converted to the free acid form by conventional procedures, for example by treatment with an inorganic acid, such as hydrochloric acid.

The non-toxic, biodegradable precursors of the compounds of formula I may be obtained by known acylation or alkylation procedures already used for the introduction of the necessary biodegradable protecting radicals. Examples of suitable acylating or alkylating reagents for incorporating a range of such protecting radicals are, for example, alkoxycarbonyl, aralkoxycarbonyl, alkoxyoxalyl and 1-(alkanoyloxy)alkyl halides, such as ethoxycarbonyl, t-butyloxycarbonyl, benzyloxycarbonyl, ethoxyoxalyl, methoxyoxalyl and pivaloyloxymethyl chloride.

The reaction may be performed under conventional N-acylation/alkylation conditions, for example in the presence of a base such as potassium carbonate or using the lithium, sodium or potassium salt of the compound of formula I, and in a suitable solvent or diluent, for example 1,2-dimethoxyethane, dibutyl ether or diethyl ether, at a temperature in the range, for example 10°–80° C.

The pharmaceutically acceptable salts of compounds of formula I may be obtained by conventional procedures, for example by reaction with the appropriate base affording a pharmaceutically acceptable cation.

When an optically active form of a compound of formula I is required, a racemic form of the said compound may be reacted with an optically active form of a suitable organic base, for example especially with an N,N,N-trialkyl-(1-phenylethyl)ammonium hydroxide such as N,N,N-trimethyl-(1-phenylethyl)ammonium hydroxide, followed by conventional separation of the diastereoisomeric mixture of salts thus obtained, for example by fractional crystallisation from a suitable solvent, for example a (1–4C)alkanol, whereafter the optically active form of the said compound may be liberated by treatment with acid using a conventional procedure, for example using an aqueous mineral acid, such as dilute hydrochloric acid.

The property of inhibiting the enzyme aldose reductase may be demonstrated in the following standard laboratory test. Thus, rats are made diabetic (as evidenced by severe glucosuria being present) by dosing with streptozotocin. The animals are then dosed daily with the test compound for 5 days. The animals are then killed and the eye lenses and sciatic nerves are removed. After a standard work-up procedure the residual sorbitol levels in each tissue are determined by gas liquid chromatography after conversion to the poly-trimethylsilyl derivatives. Inhibition of aldose reductase in vivo is then assessed by comparing the residual sorbitol levels in tissues from the dosed diabetic group of rats with those of an undosed group of diabetic rats and an undosed, normal group of rats.

A modified test may also be used in which the streptozotocin induced diabetic rats are dosed daily with test compound for two days. The animals are killed 2–4 hours after the final dose. The sciatic nerves are then removed and assessed for residual sorbitol levels as desribed above.

In general the compounds of formula I produce significant inhibition of the enzyme aldose reductase (as measured by the effects on residual sorbitol levels) in either of the above tests at an oral dose of 20 mg./kg. or less without any signs of overt toxicity or other untoward effects at the active dose or several multiples thereof. Further, preferred compounds of formula I, in general reduce the residual sorbitol level in the sciatic nerve to that in normal undosed rats when administered at an oral dose of 10 mg./kg. or less.

The property of inhibiting the enzyme aldose reductase may also be demonstrated in vitro. Thus, purified aldose reductase is isolated in known manner from bovine lenses. The percentage inhibition of this enzyme's ability in vitro to reduce aldoses to polyhydric alcohols, and particularly to reduce glucose to sorbitol, caused by a test compound is then determined using standard spectrophotometric methods. In this test the compounds of formula I in general show significant inhibition of the enzyme aldose reductase at a concentration of about $10^{-8}$M.

Compounds of formula I possessing potent inhibitory properties in this in vitro test and yet not particularly active by oral administration in the above in vivo tests may nevertheless be applied in an in vivo therapeutic or prophylactic situation, for example by topical administration direct to the tissue or organ in which inhibition of the enzyme is required, for example by topical administration to the eye. However, the compounds of formula I will primarily be administered systemically (generally by mouth) to a warm-blooded animal to produce an inhibitory effect on the enzyme aldose reductase, for example at a daily dose of 0.5 to 25 mg./kg. In man it is envisaged that a total daily dose in the range 10 to 750 mg. per man will be administered, given if necessary, in divided doses.

The compounds of formula I will normally be administered to warm-blooded animals in the form of special pharmaceutical formulations. The invention therefore also provides a pharmaceutical composition comprising a compound of formula I, or one of its pharmaceutically acceptable salts, or one of its non-toxic, biodegradable precursors, together with a pharmaceutically acceptable diluent or carrier.

The compositions may be in a form suitable for oral administration, for example in the form of a tablet, capsule, granule, dispersible powder, syrup, elixir, emulsion, suspension or gel; for parenteral administration, for example in the form of a sterile injectable aqueous suspension or solution, or oily solution or suspension; for rectal administration, for example in the form of a suppository; or for topical administration to the eye, for example in the form of an ointment, gel or sterile solution buffered at an opthalmically acceptable pH, for example in the range pH 7.0–7.6.

Topical formulations may be administered to the eye of an animal, for example man or dogs, requiring treatment for diabetic cataracts or retinopathy in a conventional manner, for example using a drop or eyewash topical formulation.

The compositions may also contain one or more other agents which are known to have a useful effect in the treatment of diabetes or galactosemia, for example a hypoglycaemic agent such as tolbutamide, chloropropamide, or glybenclamide.

The invention will now be illustrated by the following non-limiting Examples in which, unless otherwise stated:

(i) all evaporations were carried out by rotary evaporation in vacuo:
(ii) all operations were carried out at room temperature, that is in the range 18°–26° C.;
(iii) final products of formula I had satisfactory microanalyses and were isolated as their racemic (dl) forms;
(iv) petroleum ether (b.p. 60–80) is referred to as "petrol 60–80"; and
(v) yields (when given) are for illustration only and are not necessarily the maximum attainable.

EXAMPLE 1

A mixture of 1-(4-bromo-2-fluorobenzyl)-7-trifluoromethylindoline-2,3-dione (3.35 g.), potassium cyanide (1.06 g.) and ammonium carbonate monohydrate (7.8 g.) in methanol (150 ml.) and water (150 ml.) was heated at 45°–50° C. for 16 hours. The reaction mixture was cooled and a slight precipitate removed by filtration. The filtrate was acidified (2M hydrochloric acid, 80 ml.). The solid which formed was washed with water and recrystallised from tetrahydrofuran (THF)/petrol 60–80 to give 1'-(4-bromo-2-fluorobenzyl)-7'-(trifluoromethyl)-spiro[imidazolidine-4,3'-indoline]-2,2',5-trione (A) (1.98 g.), m.p. 197°–199° C.

The starting material was obtained as follows:

Anhydrous potassium carbonate (10.7 g.) and 7-trifluoromethyl indoline-2,3-dione (14.4 g.) were stirred in N,N-dimethylformamide (DMF) (100 ml.) for 30 minutes. A portion (78.9 ml.) of a 25% w/v solution of 4-bromo-2-fluorobenzyl bromide in chlorobenzene was then added and the mixture was stirred at 75°–78° C. for 2 hours. The mixture was then cooled to ambient temperature and poured into water (400 ml.). Petrol 60–80 (200 ml.) was added to the aqueous mixture and the whole was stirred for 30 minutes. The solid which formed was separated by filtration to give 1-(4-bromo-2-fluorobenzyl)-7-trifluoromethyl indoline-2,3-dione (17.8 g.), m.p. 141°–143° C.

Using the in vitro test procedure described hereinbefore, the compound A was found to produce a 50% reduction in the conversion of glucose to sorbitol in an aldose reductase preparation obtained from bovine lenses at a concentration of $1.05 \times 10^{-8}$M.

EXAMPLE 2

1'-(4-Bromo-2-fluorobenzyl)-7'-trifluoromethyl-spiro[imidazolidine-4,3'-indoline]-2,2',5-trione (51.7 g.) was added to 342 ml. of a 0.16M solution* of (1)-N,N,N-trimethyl(1-phenylethyl)ammonium hydroxide. The solution obtained was evaporated. The residue was washed with anhydrous ether (100 ml.) and then dissolved in a mixture of acetonitrile (approximately 200 ml.) and anhydrous ether (approximately 250 ml.). The solution obtained was kept at ambient temperature for 2 hours. The solid which had formed was collected by filtration, washed with cooled filtrate and then recrystallised twice from a mixture of acetonitrile and ether to give the (d)-diastereoisomeric salt of (1)-N,N,N-trimethyl(1-phenylethyl)ammonium hydroxide and 1'-(4-bromo-2-fluorobenzyl)-7'- trifluoromethyl -spiro[imidazolidine-4,3'-indoline]-2,2',5-trione (17.9 g.), m.p. 137°–140° C. (with decomposition), $[\alpha]_D^{22} + 26.3°$ (c.1.078; MeOH). This salt was mixed with methanol (105 ml.) and the suspension filtered. The filtrate was acidified with 2M hydrochloric acid (18 ml.) and water (120 ml.) was then added. The solid which was precipitated was collected by filtration, washed with the filtrate and recrystallised from aqueous methanol to give (d)-1'-(4-bromo-2-fluorobenzyl)-7'-trifluoromethyl -spiro[imidazolidine-4,3'-indoline]-2,2',5-trione (12.8 g.), m.p. 227°–229° C., $[\alpha]_D^{22} + 30.7$ (c.1.074; MeOH).

*The starting quaternary ammonium hydroxide solution was obtained by passing an aqueous solution of (1)- N,N,N-trimethyl(1-phenylethyl-)ammonium iodide (27.8 g.) through a column of anion-exchanging resin ("Amberlite" IRA401, 200 g.) newly converted into the hydroxide form ("Amberlite" is a trade-mark).

EXAMPLES 3–5

Using a similar procedure to that described in Example 1 the following compounds of formula I were obtained in racemic form:

(Example 3): 1'-(4-bromo-2-fluorobenzyl)-5'-trifluoromethyl-spiro[imidazolidine-4,3'-indoline]-2,2',5-trione, as a solid, m.p. 231°–232° C., starting from 1-(4-bromo-2-fluorobenzyl)-5-trifluoromethylindoline-2,3-dione (itself obtained as a syrup, of satisfctory purity by NMR, by reaction of 5-trifluoromethylindoline-2,3-dione and 4-bromo-2-fluorobenzyl bromide in an analogous manner to that described for the starting material in Example 1);

(Example 4): 1'-(3,4-dichlorobenzyl)-7'-trifluoromethyl-spiro[imidazolidine-4,3'-indoline]-2,2',5-trione, as a solid m.p. 170°–171° C., starting from 1-(3,4-dichlorobenzyl)-7-trifluoromethylindoline-2,3-dione (itself obtained as a syrup of satisfactory purity by NMR, by reaction of 3,4-dichlorobenzyl chloride with 7-trifluoromethylindoline-2,3-dione in an analogous manner to that described for the starting material in Example 1);

(Example 5): 1'-(2-chloro-4-bromobenzyl)-6'-trifluoromethyl-spiro[imidazolidine-4,3'-indoline]-2,2',5-trione, as a solid, m.p. 299°–301° C., starting from 1-(2-chloro-4-bromobenzyl)-6-trifluoromethylindoline-2,3-dione (itself obtained as a solid, m.p. 132°–134° C., by reaction of 2-chloro-4-bromobenzyl bromide with 6-trifluoromethylindoline-2,3-dione in an analogous manner to that described for the starting material in Example 1).

EXAMPLE 6

(All parts by weight)

A mixture of 1'-(4-bromo-2-fluorobenzyl)-7'-(trifluoromethyl)-spiro[imidazolidine-4,3'-indoline]-2,2',5-trione (50 parts), lactose (27 parts) and maize starch (20 parts), was stirred thoroughly and a paste formed from maize starch (2 parts) and water (40 parts) was added and thoroughly mixed in. The resultant mass was passed through a 16 mesh screen, then dried at 60° C. and passed through a 20 mesh screen. Magnesium stearate (1 part) was added to the granules obtained, and the whole compressed by conventional means into tablets, containing 10, 20, 50 or 100 mg. of active ingredient, suitable for oral administration for therapeutic purposes.

The active ingredient may be replaced by any other compound of formula I or a salt or non-toxic biodegradable precursor thereof.

EXAMPLE 7

(All parts by weight)

A mixture of 1'-(4-bromo-2-fluorobenzyl)-7'-trifluoromethyl -spiro[imidazolidine-4,3'-indoline]-2,2',5-trione (50 parts), calcium carbonate (20 parts) and polyethylene glycol (average molecular weight 4000) (30 parts) was vigorously stirred to obtain a uniform powdered form. This material was then charged into gelatine capsules using a conventional procedure such that each capsule contained 10, 20, 50 or 100 mg. of active ingredient suitable for oral administration for therapeutic purposes.

The active ingredient in the above procedure may be replaced by any other compound of formula I or a salt or non-toxic biodegradable precursor thereof.

Structural Formulae

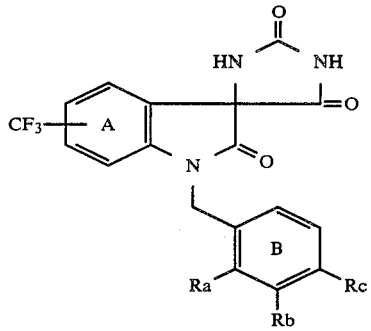

I

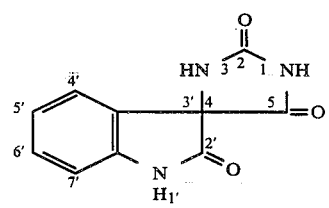

II

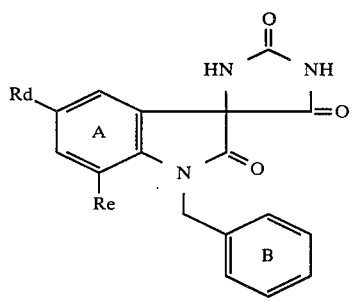

III

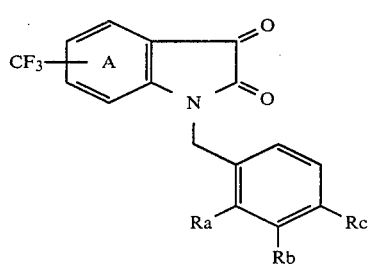

IV

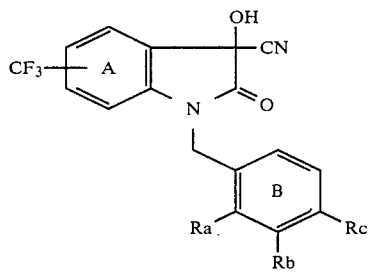

V

-continued
Structural Formulae

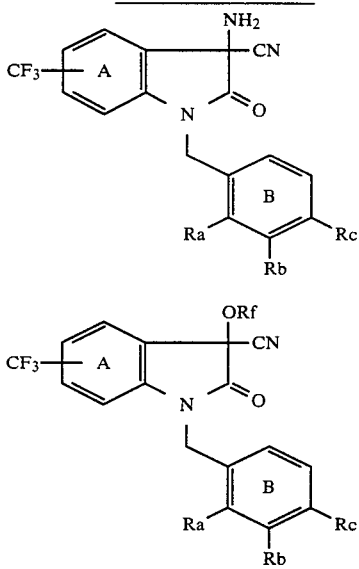

What is claimed is:

1. A compound selected from the group consisting of trifluoromethyl spiro[imidazolidine-4,3'-indoline]-2,2',5-trione of the formula I

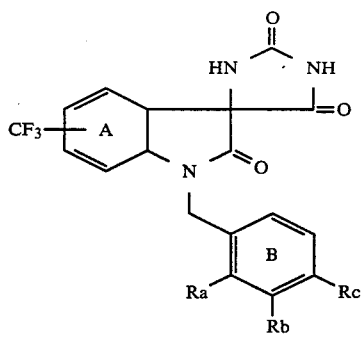

wherein the trifluoromethyl substituent in benzene ring A is located at the 7' position; and benzene ring B is dihalogenophenyl wherein Ra is fluoro or chloro, Rb is hydrogen and Rc is chloro, bromo or iodo; or Ra is hydrogen and Rb and Rc are independently chloro or bromo; and a salt with a base affording a pharmaceutically acceptable cation.

2. A compound as claimed in claim 1 wherein benzene ring B is selected from 3,4-dichloro-, 3,4-dibromo-, 3-bromo-4-chloro-, 4-bromo-3-chloro-, 4-chloro-2-fluoro-, 4-bromo-2-fluoro- and 2-fluoro-4-iodo-phenyl.

3. A compound selected from the group consisting of trifluoromethyl spiro[imidazolidine-4,3'-indoline]-2,2',5-trione of the formula III

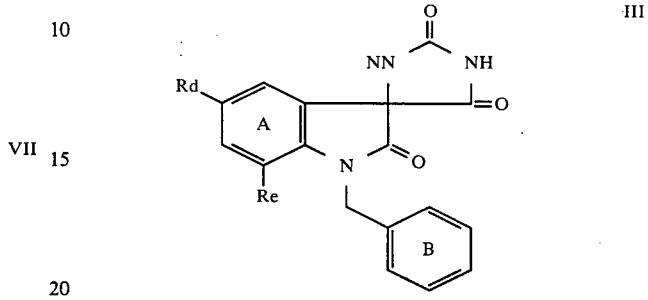

wherein benzene ring B is selected from 4-bromo-2-chloro-, 4-bromo-2-fluoro- and 2-fluoro-4-iodo-phenyl; Re is trifluoromethyl and Rd is hydrogen; and a salt with a base affording a pharmaceutically acceptable cation.

4. A compound selected from 1'-(4-bromo-2-fluorobenzyl)-7'-trifluoromethyl-spiro[imidazolidine-4,3'-indoline]-2,2',5-trione and a salt thereof with a base affording a pharmaceutically acceptable cation.

5. A compound selected from the group consisting of (d)-1'-(4-bromo-2-fluorobenzyl)-7'-trifluoromethyl-spiro[imidazolidine-4,3'-indoline]-2,2',5-trione and a salt thereof with a base affording a pharmaceutically acceptable cation.

6. A salt as claimed in claim 1 which is an alkali metal, alkaline earth metal, aluminium, or ammonium salt, or a salt with an organic base affording a pharmaceutically acceptable cation.

7. A pharmaceutical composition for use in inhibiting the enzyme aldose reductase which comprises an effective amount of a compound according to claim 1 or claim 3 with a pharmaceutically acceptable diluent or carrier.

8. A composition as claimed in claim 7 which is in a form suitable for topical administration to the eye.

9. A method of inhibiting the enzyme aldose reductase in a warm blooded animal requiring such treatment which comprises administering to said animal an aldose reductase inhibitory amount of a compound according to claim 1.

* * * * *